(12) United States Patent
Koenig et al.

(10) Patent No.: US 8,496,579 B2
(45) Date of Patent: Jul. 30, 2013

(54) METHOD AND ARRANGEMENT FOR HIGH-RESOLUTION MICROSCOPE IMAGING OR CUTTING IN LASER ENDOSCOPY

(75) Inventors: Karsten Koenig, Saarbruecken (DE); Andrei Tchernook, Limbach-Oberfrohna (DE)

(73) Assignee: JenLab GmbH, Neuengoenna (DE)

( * ) Notice: Subject to any disclaimer, the term of this patent is extended or adjusted under 35 U.S.C. 154(b) by 1675 days.

(21) Appl. No.: 11/861,472

(22) Filed: Sep. 26, 2007

(65) Prior Publication Data

US 2008/0081950 A1 Apr. 3, 2008

(30) Foreign Application Priority Data

Sep. 28, 2006 (DE) .......................... 10 2006 046 554
Sep. 29, 2006 (DE) .......................... 10 2006 046 925

(51) Int. Cl.
*A61B 1/06* (2006.01)
*A61B 18/18* (2006.01)

(52) U.S. Cl.
USPC .............................................. 600/160; 606/16

(58) Field of Classification Search
USPC .................. 606/2, 10, 11; 250/459.1, 467.1
See application file for complete search history.

(56) References Cited

U.S. PATENT DOCUMENTS

| | | | |
|---|---|---|---|
| 5,034,613 A | 7/1991 | Denk et al. | |
| 5,993,438 A | 11/1999 | Juhasz et al. | |
| 6,369,928 B1 | 4/2002 | Mandella et al. | |
| 6,485,413 B1 | 11/2002 | Boppart et al. | |
| 2004/0260148 A1 | 12/2004 | Schnitzer | |
| 2007/0081236 A1 | 4/2007 | Tearney et al. | |
| 2007/0290145 A1* | 12/2007 | Viellerobe et al. | 250/459.1 |

FOREIGN PATENT DOCUMENTS

| | | |
|---|---|---|
| DE | 100 65 146 | 7/2002 |
| DE | 101 48 783 | 10/2002 |
| DE | 10 2006 046 554 | 4/2008 |
| EP | 1 142 529 | 10/2000 |

(Continued)

OTHER PUBLICATIONS

English (machine) translation of specification of DE 10065146 to Koenig, http://translationportal.epo.org. (2002).*

(Continued)

*Primary Examiner* — Melanie Hand
(74) *Attorney, Agent, or Firm* — Frommer Lawrence & Haug LLP

(57) ABSTRACT

The invention is directed to a method and an arrangement for high-resolution microscopic imaging in laser endoscopy based on laser-induced object reaction radiation and for performing microscopic cuts in biological tissue. In using multiphoton processes for endoscopic applications in biological materials with an accuracy of under one millimeter, radiation of a pulsed femtosecond laser is focused into an object by means of a transmission focusing optics unit comprising a transmission system and miniature focusing optics having a high numerical aperture greater than 0.55 to trigger a local object reaction radiation in the micrometer to nanometer range, and the distal end of the transmission focusing optics unit is moved in at least two dimensions for highly spatially resolved scanning of the object and for transmitting object reaction radiation which is scanned in a locally progressive manner to an image-generating system with a photon detector. In an other embodiment the femtosecond laser radiation is energy enhanced is applied to the same transmission focusing optics unit to perform microendoscopic surgery in biological tissue.

30 Claims, 12 Drawing Sheets

FOREIGN PATENT DOCUMENTS

| | | |
|---|---|---|
| EP | 1 468 322 | 10/2004 |
| EP | 1 470 623 | 10/2004 |
| JP | 2003-344777 | 12/2003 |
| WO | 98/38907 | 9/1998 |
| WO | 03/056378 | 7/2003 |
| WO | 2006/004743 | 1/2006 |
| WO | WO 2006004743 A2 * | 1/2006 |
| WO | 2006/045936 | 5/2006 |
| WO | WO 2006045936 A2 * | 5/2006 |
| WO | 2006/133509 | 12/2006 |

OTHER PUBLICATIONS

König et al., Optics Express 10 (2002) 171-176 "Intratissue surgery with 80 MHz nanojoule femtosecond laser pulses in the near infrared".

König et al., Med. Laser Appl. 20 (2005) 169-184 "Nanoprocessing with nanojoule near-infrared femtosceond laser pulses".

LeHarzic et al., Optics Express 13 (2005) 6651-6656.

König, Riemann, Journal Biomedical Optics 8 (3) (2003) 432-439 "High-resolution multiphoton tomography of human skin with subcellar spatial resolution and picosecond time resolution".

Concello et al., Nature Methods 2 (12), 2005, pp. 920-931 "Optical sectioning microscopy".

Helmchen et al., (op. cit.) Nature Methods 2 (12) pp. 932-940 "Deep tissue two-photon microscopy".

Flusberg et al., (op. cit.) Nature Methods 2 (12) pp. 941-950 "Fiber-optic fluorescence imaging".

Ling Fu et al., Optics Express 14 (3), 2006, pp. 1027-1032 "Nonlinear optical endoscopy based on a double-clad photonic crystal fiber and a MEMS mirror".

König et al., Optics Express 10 (2002) 171-176.

König et al., Med. Laser Appl. 20 (2005) 169-184.

König, Riemann, Journal Biomedical Optics 8 (3) (2003) 432-439.

Concello et al., Nature Methods 2 (12), 2005, pp. 920-931.

Helmchen et al., op. cit. pp. 932-940.

Flusberg et al., op. cit. pp. 941-950 "Fiber-optic fluorescence imaging".

Ling Fu et al., Optics Express 14 (3), 2006, pp. 1027-1032.

* cited by examiner

METHOD AND ARRANGEMENT FOR HIGH-RESOLUTION MICROSCOPE IMAGING OR CUTTING IN LASER ENDOSCOPY

CROSS-REFERENCE TO RELATED APPLICATIONS

This application claims priority of German Application No. 10 2006 046 554.7, filed Sep. 28, 2006 and German Application No. 10 2006 046 925.9, filed Sep. 29, 2006, the complete disclosures of which are hereby incorporated by reference.

BACKGROUND OF THE INVENTION a) Field of the Invention

The invention is directed to a method and an arrangement for generating high-resolution microscopic imaging in endoscopy based on laser-induced object reaction radiation and for performing microscopic processing of biological material in endomicrosurgery.

b) Description of the Related Art

The invention is preferably applied in endoscopy based on multiphoton processes by means of femtosecond laser technology. In particular, it can be used in microimaging processes, laser scanning microscopy, optical coherence tomography, and single-photon and multiphoton imaging and is applied especially in endomicroscopy and endomicrosurgery due to the fact that the imaging or cutting optical system is miniaturized and made more flexible.

The invention is especially suitable for precision processing of biological materials such as for the optical deactivation of unwanted cells in tissue, surgical treatment of the ocular fundus and eye lens, treatment of implants, controlling delivery of active materials, jaw surgery, ear, nose and throat surgery, vascular surgery, lymph node therapy, heart surgery, neurosurgery, stem cell therapy, and tumor therapy.

Radiation from femtosecond lasers has been used hitherto predominantly in diagnostics. In particular, the two-photon fluorescence (see, e.g., U.S. Pat. No. 5,034,613 A) and SHG induced by near infrared (NIR) femtosecond laser radiation are used for three-dimensional microscopy of biological objects. Also, femtosecond lasers are used for diagnostics by means of optical coherence tomography (OCT) (WO 1998/038907).

NIR femtosecond lasers for optical cutting with a precision in the submillimeter range have been used commercially heretofore only for treatment of the cornea (e.g., EP 1 470 623 A2, DE 101 48 783 A1, U.S. Pat. No. 5,993,438 A). Multiphoton processes which lead to an ionization of the target, optical breakdown, plasma formation and to disruptive processes such as the formation and disintegration of cavity bubbles and the generation of shock waves are effective for this purpose and can be used for material cutting. By means of diffraction-limited focusing of the laser radiation by focusing optics having a high numerical aperture (NA>1) on illumination spots with a diameter of less than one micrometer, NIR laser pulses with low nanojoule pulse energy around the threshold for optical breakdown, typically in the range of 1 $TW/cm^2$, are sufficient for carrying out material cutting. It has been demonstrated that cutting action and drill holes in the sub-200 nm range can be realized without collateral damage through the application of multiple ~1 nJ pulses (KÖNIG et al., Optics Express 10 (2002) 171-176; KÖNIG et al., Med. Laser Appl. 20 (2005) 169-184).

Apart from applications in the field of medicine for treatment of the anterior portion of the eye, there are also femtosecond laser arrangements for precision surface machining of semiconductors and other materials (LeHarzic et al., Optics Express 13 (2005) 6651-6656).

DE 100 65 146 A1 describes a method for the analysis and optical cutting of pigmented skin tumors by means of intensive NIR femtosecond laser radiation and focusing optics having a high numerical aperture (NA). Use in the interior of the target is limited to the working distance of the macro-focusing optics with a high numerical aperture $1.2 \leqq NA \leqq 1.3$, typically 200 µm (KÖNIG, RIEMANN, Journal Biomedical Optics 8 (3) (2003) 432-439).

Thus far, there have been no commercial light endoscopes with focusing optics having a high numerical aperture. Typical numerical apertures are in the range of low $NA \approx 0.3$. In addition, all commercial light endoscopes are based on optical materials and light guides which hinder the transmission of femtosecond pulses due to high dispersion.

There are first endoscope prototypes for use on small animals that are based on GRIN lenses and microstructured light guides with relatively low NA for two-photon image generation by means of injected fluorescence markers or prior injection of foreign DNA (transfection) which lead to the formation of fluorescing proteins. Gradient index (GRIN) lenses with typical diameters of 0.2 mm to 2 mm make it possible to construct miniaturized systems. Thanks to their planar end faces, multi-lens systems can be produced simply and compactly. The NA depends on the material that is used and on the manufacturing process of the refractive index gradient. Silver-doped GRIN lenses have a maximum NA of 0.48 (NIR at 850 nm) and thallium-doped GRIN lenses have a maximum NA of 0.55 (850 nm). However, the resolution, excitation efficiency and detection efficiency are low due to the low NA.

Extremely high laser pulse energies are required to achieve the light intensity needed for multiphoton-based removal of material which is substantially higher than the light intensity for diagnostics. This would require cost-intensive, elaborate laser apparatus. Further, there would be a high risk potential. A cutting precision in the sub-100 µm range within the target could not be achieved because of collateral damage, including the formation of large cavity bubbles in a range greater than a cell dimension and uncontrolled auto-focusing (collateral damage correlates to the pulse energy).

All of the methods and arrangements mentioned above have the disadvantage that they cannot be applied for endoscopic use of multiphoton processes by means of the radiation of a femtosecond laser inside materials and within the body for precision image generation and/or cutting with an accuracy of under one millimeter.

The development of a number of microscopic optical imaging methods (so-called microimaging) such as laser scanning microscopy (LSM), optical coherence tomography (OCT) and multiphoton imaging (MPI) has revolutionized optical microimaging and has rapidly expanded its possibilities (see, e.g., Concello et al., Nature Methods 2 (12), 2005, pages 920-931; Helmchen et al., op. cit. pages 932-940). Devices based on these methods are used increasingly in biomedicine because they permit microscopic examinations which are fast, noninvasive and do not use contrast agents (see, e.g., Flushberg et al., op. cit. pages 941-950).

At the present time, optical microscopic scanning methods are mostly used for external or near-surface examinations because flexible, miniaturized devices have not succeeded in scanning methods due to the absence of miniaturized scanners.

Existing optically imaging solutions such as, e.g., LSM endoscopes according to EP 1 468 322 have only a limited resolution and can only be used for LSM. MPI endoscopes (e.g., Ling Fu et al., Optics Express 14 (3), 2006, pages 1027-1032) intrinsically have relatively large dimensions due to the fact that a MEMS (micro-electromechanical system) mirror scanner with good optical parameters is not smaller that about 3 mm (so that an endoscope with MEMS cannot have a diameter of less than approximately 5 mm).

OBJECT AND SUMMARY OF THE INVENTION

It is the object of the invention to find a novel possibility for endoscopic application of multiphoton processes which permits a precise imaging and/or microcutting of materials, particularly biological materials, with an accuracy of under one millimeter by means of femtosecond laser radiation.

Another object of the invention is to find a possibility for microscopically scanning optical imaging, particularly for flexible medical hand-held instruments and microendoscopes, which permits an optical head having a high spatial resolution to be miniaturized and flexibilized without being limited to a particular imaging and analyzing method (e.g., MPI, OCT or LSM).

An extended object consists in the flexible application of the miniaturized optical head for microscopic processing of biological and other materials and for combined imaging and cutting devices.

According to the invention, the object is met in a method for generating high-resolution microscope images in the microendoscopy based on laser-generated object reaction radiation characterized by the following steps:
 focused excitation radiation is pulsed from a laser system into an object by means of a transmission focusing optics unit comprising a transmission system and miniature focusing optics which have a high numerical aperture greater than 0.55 and are rigidly connected to the end of the transmission system to trigger a local reaction radiation of the object in the micrometer to nanometer range,
 the distal end of the transmission focusing optics unit executes a scanning movement in at least two dimensions for the successive spatially changed orientation of the excitation radiation relative to the object and object reaction radiation of the object present at the distal end of the miniature focusing optics is scanned in high resolution in a locally allocated manner, and
 the object reaction radiation which is scanned in a locally progressive manner is transmitted by the transmission focusing optics unit to an image-generating system with a photon detector.

A third scanning process is advantageously carried out orthogonal to the two-dimensional scanning movement by axial movement of the transmission focusing optics unit for changing the depth of an image recording of the object reaction radiation generated from the two-dimensional scanning movement into a focal plane predetermined by the miniature focusing optics.

The miniature focusing optics and micro-optics which are associated with the laser system and image-generating system and which produce a direct optical coupling with the laser system and the image-generating system are advisably moved in a scanning motion simultaneously as a transmission focusing optics unit by means of a rigid connection, and a relative movement can be carried out in axial direction for adjusting the depth of the focal plane in the object. The focal plane is advantageously varied by varying the distance between the transmission system and the miniature focusing optics.

In a preferred variant, the miniature focusing optics and an optical fiber which produces an optical coupling with the light-conducting fiber are moved simultaneously as a transmission focusing optics unit in a scanning manner by means of a rigid connection. Multi-channel scanning of the object can be carried out simultaneously by a kind of fiber bundle comprising a plurality of fiber focusing optics units, or imaging and cutting functions can be carried out on the object in a quasi-simultaneous manner in that the excitation radiation is used for tissue cutting by changing parameters in one channel.

The extended object of the invention is met according to the invention in that:
 the excitation radiation is switched to an increased-output active radiation,
 the active radiation which is focused by means of the transmission focusing optics unit is pulsed into the object for triggering local tissue changes, and
 the distal end of the transmission focusing optics unit is moved in a defined manner for carrying out three-dimensional cutting steps in the object.

The radiation of an NIR femtosecond laser is transmitted into the object virtually without dispersion by means of miniature optics with a high numerical aperture, particularly GRIN optics, preferably in combination with flexible optical light guides, reflective waveguides or rigid, rod-shaped GRIN optics, and is focused on an illumination spot of less than 100 µm, preferably 1 µm, on a target. In a focal plane, the femtosecond laser can also cut biological tissue when the transient intensity is in the range of greater than 100 GW/cm$^2$, typically in the range of 1-20 TW/cm$^2$.

By shifting the focal plane, e.g., by means of a piezo-driven adjusting unit, the focal plane can be varied and material cutting can accordingly be made possible at various target depths. The pulse width at the target is advisably less than 10 ps, preferably less than 400 fs. Because of the low absorption coefficient and scattering coefficient in the NIR range, an NIR laser wavelength is preferred. However, the invention also includes laser wavelengths in the visible region, particularly the frequency-doubled radiation of a femtosecond laser generated by an SHG crystal and radiation in the UV region, particularly THG laser radiation.

Laser pulses with repetition frequencies in the MHz range, but also with a lower repetition frequency (e.g., in the kHz range), and individual pulses can be used for cutting. Exposure times of less than 10 ms per illumination spot are usually sufficient for material cutting.

Switching for beaming in the increased-output active radiation for tissue cutting of the object is advantageously carried out alternately with the scanned beaming in of reduced-output excitation radiation for spatially-resolving image recording of object reaction radiation. The radiation emitted by the object is advisably detected by means of time-correlated single-photon counting.

Further, in a method for micro-processing of biological material, particularly skin tissue, in laser endoscopy with a precision under one millimeter, the object of the invention is met in that laser pulses of a femtosecond laser with a pulse energy of from 0.05 nJ to 100 µJ are coupled via the fiber into the miniature focusing optics being arranged on the object side and having a high numerical aperture, and are focused on a target inside the object with an illumination spot of less than 10 µm, in that the laser pulses with transient intensities greater than 100 GW/cm$^2$ trigger multiphoton processes in the form of a target ionization, an optical breakdown and plasma formation which are used for endoscopic micro-processing with an accuracy under 100 μm without the occurrence of significant collateral damage in neighboring areas, and in that the plasma radiation emitted by the target and other object reaction radiation emitted by the target is detected in an image-generating manner by an illumination and detection device, particularly by a multiphoton laser microscope, in order to monitor the micro-processing.

In this way, individual cells within tissue can be destroyed optically without damaging neighboring cells, the diameter of the destroyed area being varied by selecting the exposure time and the laser pulse energy that is used. A precise cut with cut widths of less than 10 μm can be carried out in the interior of an object by means of linear movement accompanied by conditioning. The width of the cut is varied through the selection of exposure time and laser pulse energy.

When a region of interest (ROI) is systematically scanned, a precise removal of material can be realized on larger areas of 100 μm² to 1 mm² with a precision of under 10 μm and a depth action of under 20 μm. By further displacing the focal plane, it is possible to realize a large-volume material removal in the range of 1 μm³ to 1000 mm³.

The radiation emitted by the target during the laser cutting, particularly the plasma light, can be received and transported via the same beam path as the laser radiation (flexible microstructured fibers, reflective waveguides, GRIN optics) and via the focusing optics and coupled out by beam splitters for detection. Further, at intensities below the optical breakdown threshold, typically in the range of 1-100 GW/cm², by scanning the object, an image recording can be achieved through detection of the two-photon and three-photon fluorescence and the SHG and THG of determined object structures, e.g., collagen fibers. In this way, the target to be cut can be found in a precise manner. Often the SHG and autofluorescence can be used for the target search without additional marking of the object. Further, this image generation can be used immediately after irradiation with intensive laser pulses in the TW/cm² range to show the effect of the laser cutting in an image-generating manner. Interestingly, it was observed in preliminary trials that cut biological material emits an intensive luminescence in the area of the laser cutting.

Further, in a miniaturized microscopic head for endoscopic applications in which transmission optics for supplying an excitation radiation, focusing optics for introducing bundled excitation radiation into an object, and a scanning device for changing the location of the energy input are arranged in a housing, wherein the focusing optics focus the active radiation into the object through a window in the housing, the above-stated object is met in that the focusing optics are miniature focusing optics which have a diameter of less than 6 mm and a numerical aperture of NA>0.55, wherein the excitation radiation is focused by the miniature focusing optics so as to be limited locally on an area of less than 100 μm in the object, in that the end of the transmission optics in the housing is rigidly connected to the miniature focusing optics and forms a transmission focusing optics unit, and in that the scanning device has at least one scan actuator for lateral movement of the miniature focusing optics in the immediate vicinity of the window, which scan actuator is movable in two dimensions in a plane.

Further, the scanning device advisably has an axially movable adjusting unit for axial movement of the transmission focusing optics unit, wherein the transmission focusing optics unit is clamped in the adjusting unit so as to be secured axially. In a first variant, the transmission focusing optics unit is rigidly assembled from the miniature focusing optics and an optical fiber, wherein the transmission focusing optics unit is clamped in the adjusting unit so as to be fixed axially. In a second variant, a reflective waveguide is used instead of the optical fiber. In a third variant, it comprises the miniature focusing optics and the microscope optics of a illumination and detection device, wherein the two-dimensional scan actuator and the axial adjusting unit are connected exclusively to the miniature focusing optics.

The miniature focusing optics are preferably multi-lens GRIN optics which either have a rounded end face or are preceded by a refractive spherical lens segment in order to achieve the high numerical aperture of NA>0.55 (up to NA=0.85). To further improve axial resolution, the focusing optics advisably contain two-lens GRIN optics and diffractive optics arranged therebetween.

The scanning device of the two-dimensional scan actuator is advantageously constructed as a piezo scanner. However, it can also advantageously be constructed as an electrostatic scanner or as an electromagnetic scanner. To realize a three-dimensional scanner, the axial adjusting unit is connected to the two-dimensional scan actuator and the scan actuator is fastened in an axially movable scanner holder.

The transmission optics advantageously comprise a microstructured photonic crystal fiber (PCF) because this transmits the femtosecond laser radiation virtually without dispersion. A double-clad large-area core PCF type fiber is preferably used for spatially resolved image recordings. For other applications, the fiber is formed as a large-area core PCF.

At least one photoreceiver is advantageously arranged around the fiber in the scanner housing for directly receiving the object reaction radiation. The photoreceiver is preferably provided with an optical filter combination. A plurality of photoreceivers can advantageously be arranged around the fiber in the housing for directly receiving different components of the object reaction radiation.

In order to achieve multichannel scanning, a plurality of fibers are advantageously guided in parallel in a fiber holder in the housing. The fibers are advisably embedded in a flexible band and have stiffening elements for suppressing oscillation.

The housing is preferably tubular and is hermetically sealed at its end sides by a cover and a window. Particularly for endoscopic applications, the housing has at least one plane side wall, a window is arranged laterally in the plane side wall of the housing and the housing is hermetically sealed with end covers. For this construction, the miniature focusing optics have a radiation-deflecting element so that the excitation radiation exits laterally from the transmission focusing optics unit and can be focused on the object through the laterally arranged window. The axial adjusting unit is provided for a first lateral scan dimension at the object and the scan actuator is provided for a second lateral scan dimension and for the depth scan at the object. The hermetically sealed housing is advisably evacuated in order to ensure unimpeded movement of the distal end of the transmission focusing optics unit.

The invention is based on the idea that conventional endoscopic image recorders or microsurgical units have either an optical resolution that is too low or dimensions that are too large or are tied to a particular microscopic process for imaging so that biological tissue can only be imaged based on certain characteristics. The devices are also difficult to combine with optical cutting arrangements.

Also, endoscopic image recorders with GRIN optics have been successful, but further miniaturization is hampered in that the scan deflection angle and, therefore, the lateral resolution are very limited. Further, the optical heads are actually adapted to and applicable to only one of the microscopic imaging methods (MPI, LSM, and so forth).

The invention solves these diverse problems in that the scan angle of the radiation in front of the focusing optics which was previously insufficient is realized by two-dimensional or three-dimensional scanning of focusing optics which are rigidly connected to the light-guiding fiber, and the fiber-coupled focusing optics are scanned as an integral part by an actuator via a thin optical window. The active radiation (i.e., the excitation radiation for one of the image-generating methods mentioned above) is coupled out of the fiber through these focusing optics and focused into the object by the focusing optics, and reaction radiation that is projected back from the object is collected again by the focusing optics and guided via the proximal end of the focusing optics to an image sensor so as to be adapted to the numerical aperture of the light-guiding fiber. Different focusing optics (for MPI or LSM, e.g., with a high numerical aperture (NA>0.5) at the distal end) are used depending on the imaging method.

The actuators which are used and which enable two-dimensional scanning patterns are, for example, miniaturized piezo actuators, electrostatic actuators, or electromagnetic actuators. The distance of the distal end of the focusing optics from the window and the window thickness are adapted to the working distance of the focusing optics (i.e., their distal focal length) and take into account changes in the distance from the window for the depth adjustment of the fiber-coupled focusing optics. During lateral scanning of the fiber focusing optics combination, points on a preselected plane of the object are progressively scanned in a systematic manner. The object reaction radiation, e.g., fluorescence or SHG (second harmonic generation), which is generated after the action of the active radiation is transmitted to a sensor unit by the focusing optics and a light-conducting fiber.

The second extended object of making the invention more flexible for applying different imaging methods is achieved in that the (optical) active radiation of a light source is transported through a flexible light-conducting fiber to the object to be imaged and is used for scanning the object, and the reaction radiation is picked up again by the light-conducting fiber (so-called direct scanner). Different optical fibers (transporting fibers) are required depending on the imaging method that is used. For example, PCF (photonic crystal fibers) are used for MPI. The scan head can accordingly be used with other imaging methods by connecting different fibers.

An active radiation (excitation radiation) is guided to the object through the fiber and focused on the surface or at a depth in the object by the focusing optics, and a reaction radiation coming back from the object is guided through the optical window by the focusing optics to an external sensor unit or to a sensor unit that is located directly in the scanner housing.

A direct scanner provided in this way can achieve high axial and lateral resolution of the object imaging in the micrometer range. In addition, the scanner can be used in microsurgery and nanosurgery and as a guided cutting tool for cutting different tissues and materials by using the active radiation through a substantially increased output for laser cutting or cutting processes and switching alternatively for observation.

The solution according to the invention makes possible novel endoscopic applications of multiphoton processes which permit a precise image generation and/or micro-cutting of materials, particularly of biological materials, with an accuracy of under one millimeter by means of the radiation of a femtosecond laser. A miniaturized microscopic receiving head, particularly for flexible hand-held medical instruments and microendoscopes, makes it possible to obtain images that are scanned at high resolution for different image-generating methods, preferably for multiphoton imaging (MPI) and laser scanning microscopy (LSM), with substantially smaller, lighter and more flexible measuring heads and to open up the MPI method (e.g., in endoscopy) for micro-cutting processes with the same arrangement and to combine it with other imaging methods.

The invention will be described more fully with reference to embodiment examples.

DESCRIPTION OF THE PREFERRED EMBODIMENTS

The method according to the invention will be described in the following—without limiting its universality for the application of other laser-assisted imaging methods—with reference to a femtosecond laser microscope such as is used for single-photon, two-photon and multiphoton microscopy.

Figure 1:
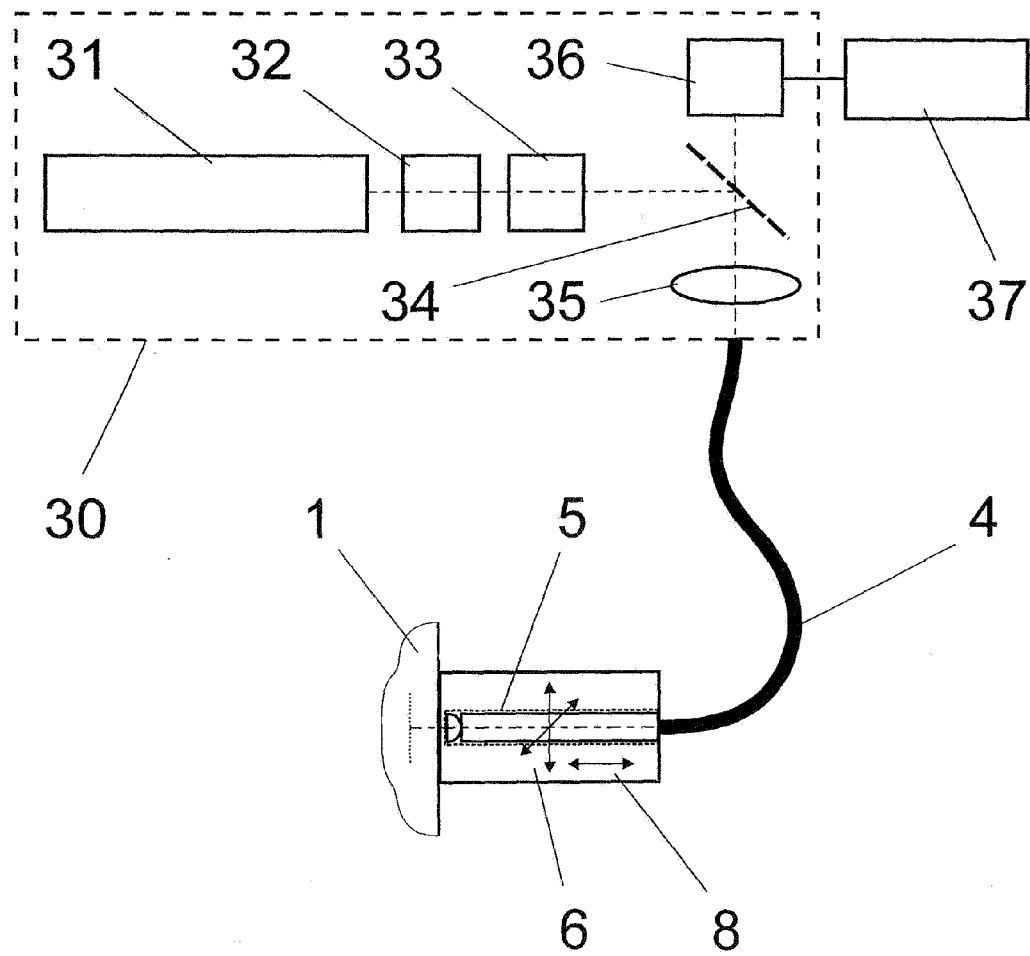
FIG. 1 shows a basic construction for carrying out the method according to the invention based on a illumination and detection device with a very high numerical aperture for femtosecond laser cutting and observation of cutaneous tissue.

As is shown in FIG. 1, the arrangement comprises an illumination and detection device 30 in which pulsed radiation with an emission wavelength of 780 nm generated by an 80-MHz titanium-sapphire femtosecond laser 31 is transmitted through a shutter 32, a beam attenuator 33 and a dichroic splitter mirror 34 and provided in a focused manner by microscope optics 35 and in which a secondary radiation (e.g., single-photon, two-photon or multiphoton fluorescence, SHG, THG, luminescence, etc.) returning from an object 1 through laser excitation is coupled out through the splitter mirror 34 to a photon detector 36.

The microscope objective 35 of the illumination and detection device 30 couples the laser radiation into the central area 20 (shown only in FIG. 10) of a multimode optical fiber 4 which is constructed as a microstructured photonic crystal fiber (PCF), preferably as a double-clad fiber, and takes over the transmission of radiation to miniature focusing optics 5 with a high numerical aperture (NA>0.55).

The miniature focusing optics 5 which are rigidly arranged at the distal end of the fiber 4 are special miniature GRIN optics comprising rod lenses with a radial gradient refractive index coupled with refractive lens shapes for achieving a high numerical aperture (NA) in order to provide a focusing on an irradiation spot less than 1 μm. For this purpose, the distal lens is shaped as a half-sphere or a refractive half-spherical lens segment 5' is arranged in front of the GRIN optics. Typical dimensions for these special miniature focusing optics 5 are an outer diameter of 1.7 mm and a length of around 2 cm.

After actuation of the shutter 32, NIR laser pulses are applied to the object 1 to be cut through the miniature focusing optics 5 initially with a pulse energy of 0.5 nJ which has been reduced by the attenuator 33. Surfaces at different depths in the tissue can be scanned by a scanning unit 6, preferably in the form of a piezo actuator 6' (according to FIG. 2), for controlled x-y deflection (vibration) and by an axial adjusting unit 8 for varying the focal plane. Signals emitted from the object 1 in the form of SHG radiation and two-photon fluorescence are detected by the miniature GRIN optic 5, guided to the dichroic splitter mirror 34 primarily in the outer cladding of a PCF fiber 4 via the microscope optics 35, and transmitted from the dichroic splitter mirror 34 to a photon detector 36, typically a photomultiplier (PMT).

A three-dimensional imaging of the object 1 can be produced by image processing at a computer 37 (e.g., PC) by linking the signals of the photon detector 36 to the x-y scan position and the focal plane. Based on this imaging, a target can be defined within the object 1. The laser beam is positioned on the target and, after adjusting a high pulse energy of, e.g., 3 nJ by changing the transmission of the attenuator 33 (e.g., by a change in position) and after opening the shutter 32, is suitable to generate a local plasma in the focal plane within the object 1. This local plasma can be used for drilling (by means of single-point illumination), cutting (by line scan) and for deactivating an individual cell or for ablation by scanning a region of interest (ROI).

A signal of plasma radiation is registered at the photon detector 35 during the cutting process. At the conclusion of the cutting process, the object 1 can be scanned again by laser pulses of low pulse energy (e.g., 0.5 nJ) in order to obtain an image based on the SHG signal, the two-photon fluorescence or the luminescence of the cut area.

In a particularly advantageous manner, a fiber 4 with a centrally located PCF light guide for transmitting the laser pulses and with peripherally extending light guides, which need not be microstructured, is used for transmitting the object radiation. Further, instead of miniature focusing optics 5 with a spherical lens segment 5', GRIN optics with only two lenses can also be used to generate a high NA. In another modified construction, miniature GRIN optics with a high NA due to additional curvature of the distal end face (which is otherwise usually plane) are used.

In a special application for examining human skin, miniature focusing optics 5 with a high NA are, in addition, rigidly coupled to a commercial two-photon microscope or a commercial multiphoton tomograph—both are included herein under the term illumination and detection device 30—in such a way that the focal plane defined by the microscope optics 35 of the illumination and detection device 30 (multi-photon microscope or tomograph) is transmitted by the miniature focusing optics 5 to deeper layers of the object 1 to be cut. In this way, the focus can be transmitted into the interior of the object 1, for example, by means of rod-shaped miniature GRIN optics 5 which have a length of 2 cm and a very high numerical aperture of NA>0.6 (up to 0.85) through a curved GRIN lens surface or a spherical lens segment 5' and which are located in a special stainless-steel tube with a sapphire window (window thickness of less than 200 μm) and arranged at a triaxial adjusting device (cooperation of lateral scan actuator 6 and axial adjusting unit 8). The distance from the microscope optics 35, and therefore approximately from the focal plane in the object 1, can be shifted by means of the axial adjusting unit 8 typically in a range up to 0.5 mm with a precision in the submicrometer range.

The radiation emitted by the object 1 is captured by the miniature focusing optics 5, detected via the microscope optics 35 and the dichroic splitter mirror 34 by means of photon detectors 36 which are located inside the illumination and detection device 30 (multi-photon microscope or tomography), and used for image generation.

After transmission through shutter 32, attenuator 33 and dichroic splitter mirror 34, the radiation of a femtosecond laser 31 is coupled by an optical articulated arm, x-y galvosscanner and optics (not shown) into high-NA endoscopic, rigid miniature focusing optics 5 which are movable by means of an axial adjusting unit 8 for varying the focal plane and which are enclosed by a fiber bundle 4. The cutting is carried out by means of radiation of high pulse energy which is transmitted through the miniature focusing optics 5, while the radiation emitted by the object 1 is detected through the miniature focusing optics 5 and guided to the photon detector 36 through the surrounding fiber bundle 4.

The photon detector 36 should be characterized by a fast response time so that the arrival of the photons of the radiation emitted by the object 1 is detected in a time-correlated manner, preferably by means of time-correlated single-photon counting. A temporal resolution in the range of a few picoseconds can be achieved in this way and can be used for determining the fluorescence lifetime and for separating the SHG/THG radiation and plasma radiation from the fluorescence. Further, the photon detector 36 can be constructed as a spectral detector by combining a PMT array with a polychromator.

In another group of constructions, the arrangement for high-precision positioning of the laser radiation and detection of the object reaction radiation is based on a commercially approved illumination and detection device 30 (such as, e.g., a MPI laser microscope) combined with a direct scanner which is implemented as a handle part that is coupled endoscopically by an optical fiber 4.

Figure 2A:
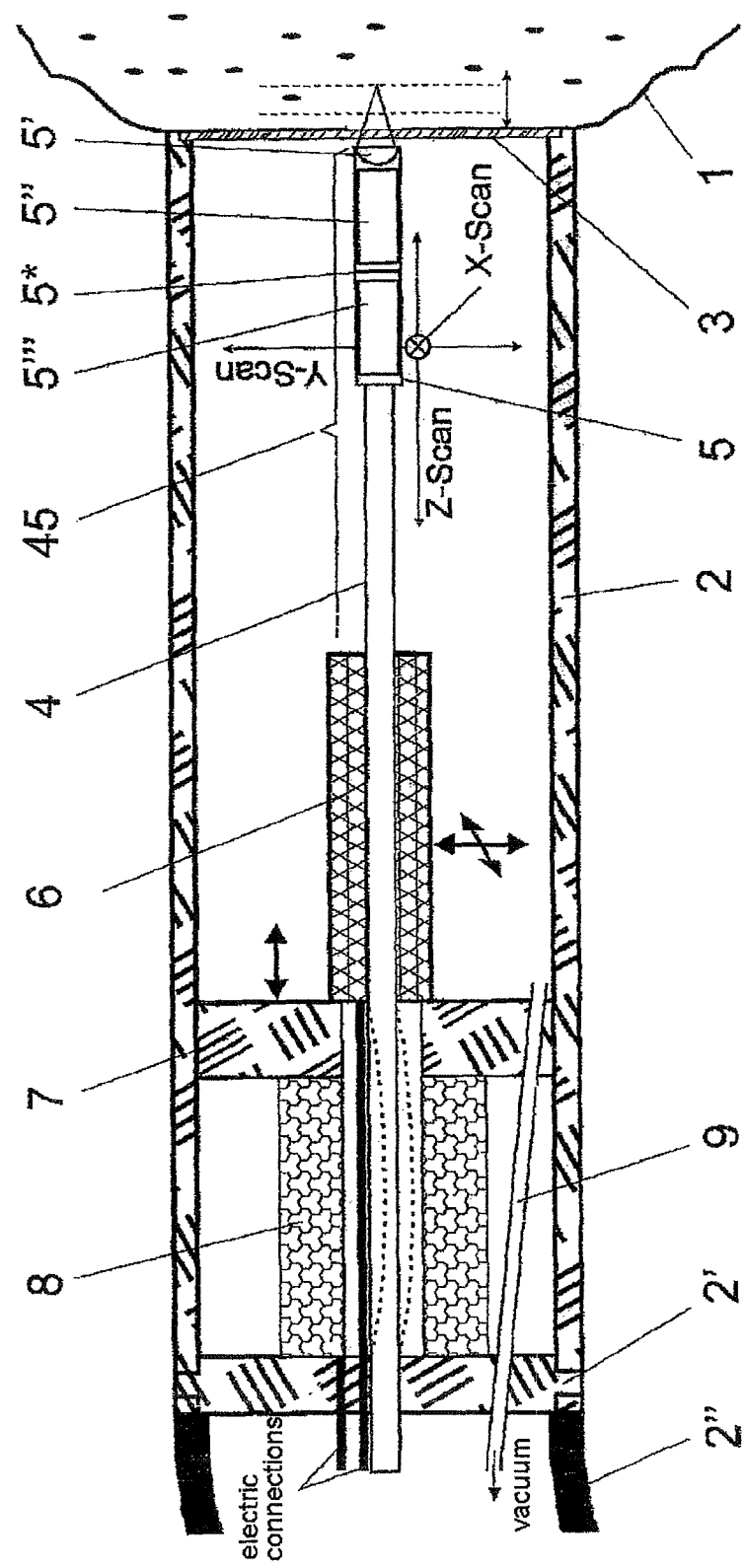
FIG. 2a shows a direct scanner with a piezo actuator for axial scanning and detection of fluorescence through an optical fiber (double-clad fiber)

As is shown schematically in FIG. 2a, this arrangement basically comprises a hand-held rigid housing 2 which is placed on an object 1 by a window 3 which is transparent for the optical radiation components being used, miniature focusing optics 5 which are coupled to an optical fiber 4, and a scan actuator 6 which moves the rigidly connected fiber focusing optics arrangement 45 in two dimensions (x-y scan) in a freely selectable scanning pattern. An axially movable scanner holder 7, which makes possible a third scanning movement (z-scan) orthogonal to the first two scan directions by means of an axial adjusting unit 8, is provided inside the housing 2. The housing 2 is covered by a housing cover 2' preceded by a flexible tube 2" for supply lines, e.g., for fibers 4 (for supplying active radiation or reduced-output excitation radiation and transmitting object reaction radiation), electrical leads for the scan actuator 6 and adjusting unit 8 and, optionally, a vacuum line 9.

Various operating modes and structural modifications which are described in the following as separate embodiment examples can be realized based on this basic variant.

1. Direct Scanner with Three-Dimensional Scan

In this example, as is shown in FIG. 2a, the direct scanner comprises miniaturized focusing optics 5, a fiber 4 whose distal end is connected to the proximal end of the focusing optics 5, and a scan actuator 6, e.g., a piezo actuator 6', which scans the distal end of the miniature focusing optics 5 directly via a thin optical window 3 contacting the object 1. The focal point of the focusing optics 5 is located behind the window 3 on the surface of the object 1 or at a depth therein and is scanned (x-y scan) by the miniature focusing optics 5. The scan depth in the object 1 can be adjusted by an axial adjusting unit 8. The axially movable scanner holder 7 to which is fastened the scan actuator 6, which jointly moves the fiber 4 and focusing optics 5 laterally, is displaced in axial direction. Accordingly, the distance between the distal end of the focusing optics 5 and the window 3 changes and carries out a z-scan in longitudinal direction of the housing 2. The free length of the fiber 4 within the axial adjusting unit 8 and the scanner holder 7 is used for compensating the length of the fiber 4 when changing the distance of the fiber focusing optics 45 relative to the window 3.

The miniature focusing optics 5 can have a diameter that differs from that of the fiber 4 and can be constructed as GRIN optics, conventional optics, Fresnel optics, or a combination of GRIN optics and other optics (diffractive optics, Fresnel optics, etc.).

In a particularly advantageous construction, the miniature focusing optics 5 have a refractive spherical lens segment 5' whose distal surface is planar, two GRIN lenses 5'' and 5''', and diffractive optics 5* arranged therebetween. The object-side GRIN lens 5'' serves to compensate for aberrations of the spherical lens segment 5' and generates quasi-parallel or slightly divergent beam bundles at its proximal end from the highly divergent object reaction radiation transmitted through the spherical lens segment 5'. The second GRIN lens 5''' serves to couple this radiation into the fiber 4 and to couple the active radiation (excitation radiation) out of the fiber 4. The diffractive optics 5* correct chromatic aberrations of the spherical lens segment 5' and of the GRIN lenses 5'' and 5'''.

The housing 2 which is made of medically compatible material is hermetically sealed (vacuum-tight) at its distal end by the optical window 3 which is also made of medically compatible, transparent material. At its proximal end, the housing 2 for medical applications is terminated by the cover 2', likewise in a vacuum-tight manner. The cover 2' is connected to the tube 2'' with all of the lines necessary for the scanner operation. The axial adjusting unit 8 is fastened to the distal side of the cover 2'. The cover 2' ensures that all of the lines leading to the scanner are guided through in a vacuum-tight manner.

The housing 2 can be evacuated by the vacuum line 9 in order to reduce the air resistance for the distal end of the fiber focusing optics unit 45 during scanning.

The axial adjusting unit 8 can be constructed, e.g., as a piezo actuator. Accordingly, the direct scanner can execute any combination of x, y and z movements for point scanning, line scanning, two-dimensional scanning or three-dimensional scanning. This is achieved by a task-oriented controlling of the two-dimensional scan actuator 6 and of the axial adjusting unit 8.

Figure 2B:
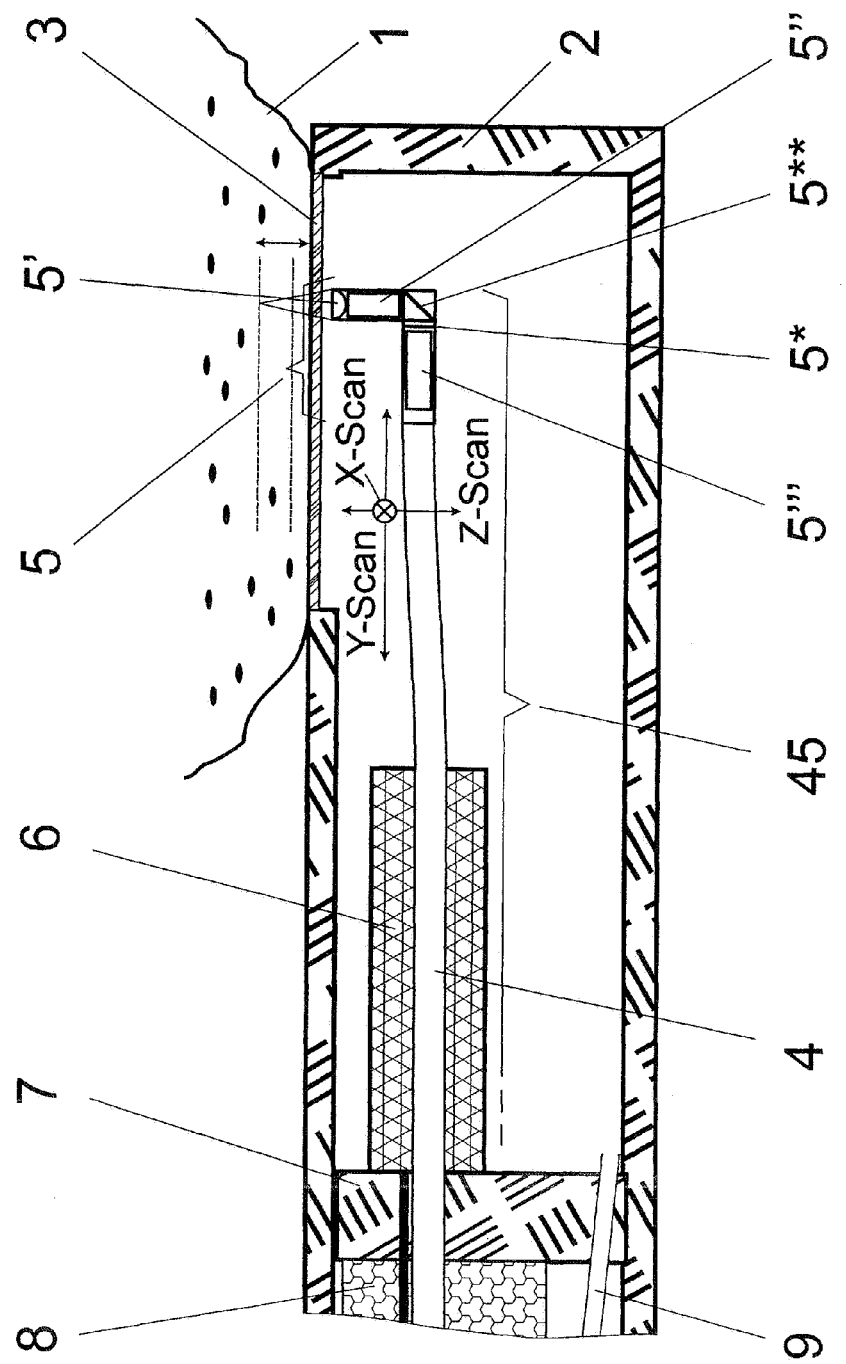
FIG. 2b shows a direct scanner with a piezo actuator for lateral scanning and detection of fluorescence through an optical fiber (double-clad fiber)

FIG. 2b shows a special construction of the direct scanner with an optical window 3 which is arranged laterally at a wall of the housing 2. In this instance, the focusing optics 5 contain a deflecting element 5** (e.g., a prism) which deflects the direction of the radiation by about 90°. Accordingly, the depth adjustment with respect to the object 1 (z-scan) in this constructional form of the direct scanner is taken over by the piezo actuator 6' which executes the x-scan in exactly the same way as in FIG. 2a. The axial adjusting unit 8 takes over the y-scan in this case.

Figure 3:
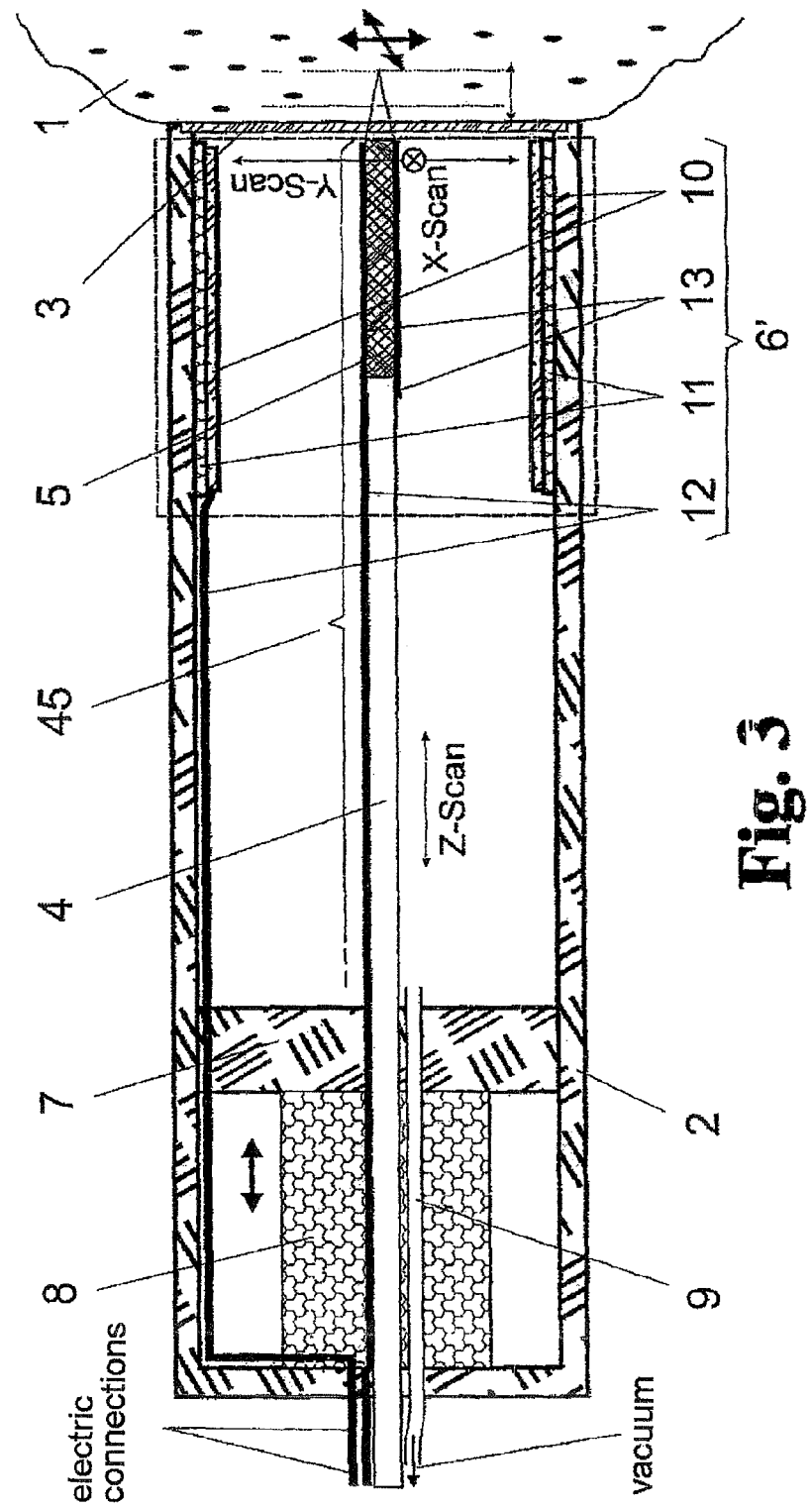
FIG. 3 shows a direct scanner according to FIG. 2a with an electrostatic actuator.

FIG. 3 shows a modified construction of the direct scanner with an electrostatic scanner 6''. In this case, the fiber focusing optics unit 45 is moved and adjusted in that a conductive coating 13 which receives electric potential via line 12 undergoes a directed action through the electric field of the oppositely located layer electrodes 10. The layer electrodes 10 are arranged directly on the inner wall of the housing 2 in case the housing 2 is made of insulating material or rest on an insulating substrate 11 when—as is shown in FIG. 3—the housing 2 is made of conductive material. In other respects, the direct scanner with the electrostatic actuator 6'' functions according to the same scheme as the piezo actuator 6'.

Figure 4:
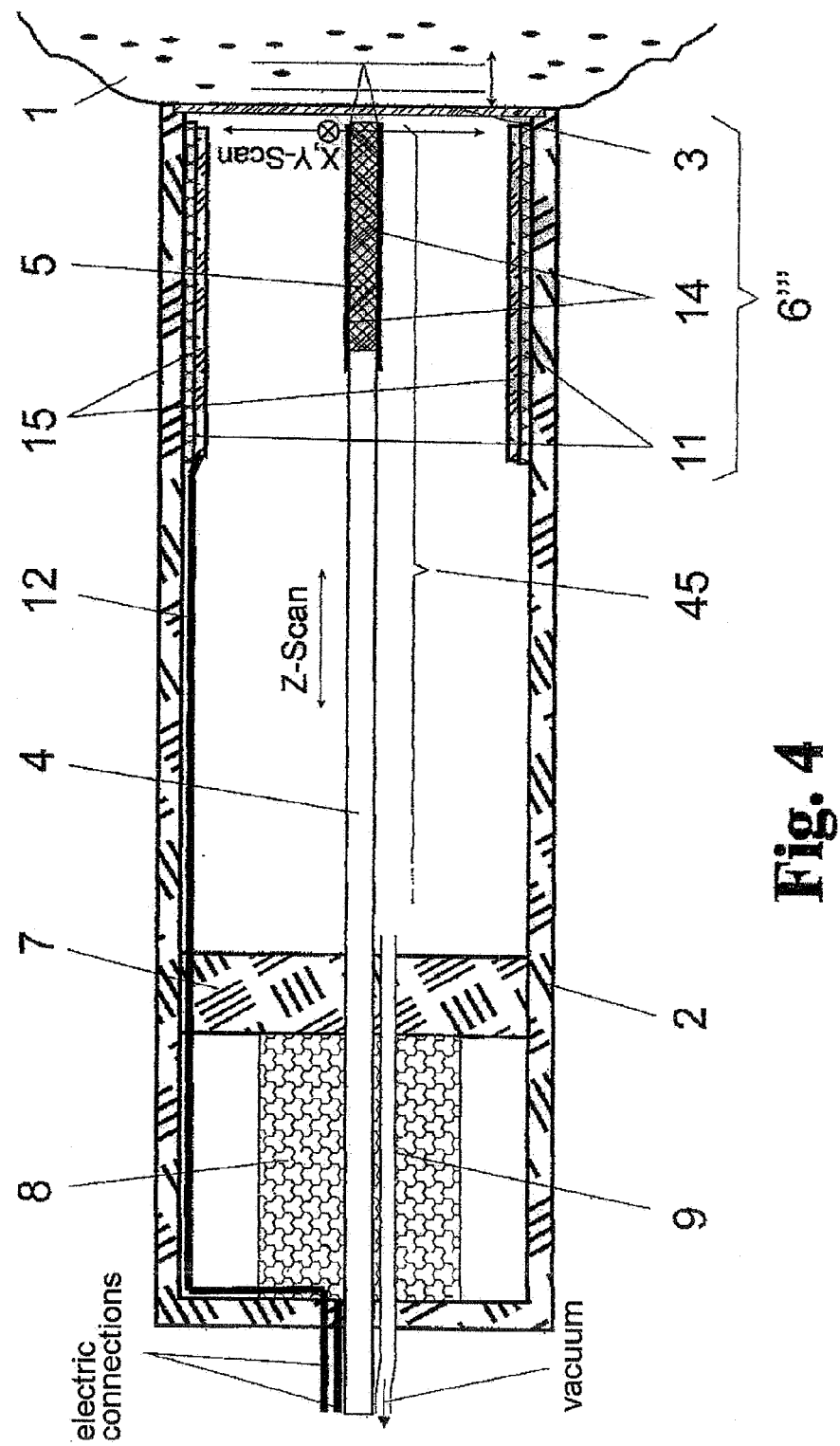
FIG. 4 shows a direct scanner according to FIG. 2a with an electromagnetic actuator and a permanent magnet on the fiber arrangement.

FIG. 4 shows a modified construction of the direct scanner with an electromagnetic actuator 6''' in which a permanent magnet 14 is used. In this case, the fiber focusing optics unit 45 is moved and adjusted in that the permanent magnet 14 which is arranged on the fiber focusing optics unit 45 (e.g., as a ferromagnetic coating) undergoes a directed action through the electromagnetic field of the oppositely located current-conducting inductive elements 15 which are arranged at the inner wall of the housing 2. In case the housing 2 is made of conductive material as in FIG. 3, an insulating substrate in the form of a dielectric layer 11 is used.

Figure 5:
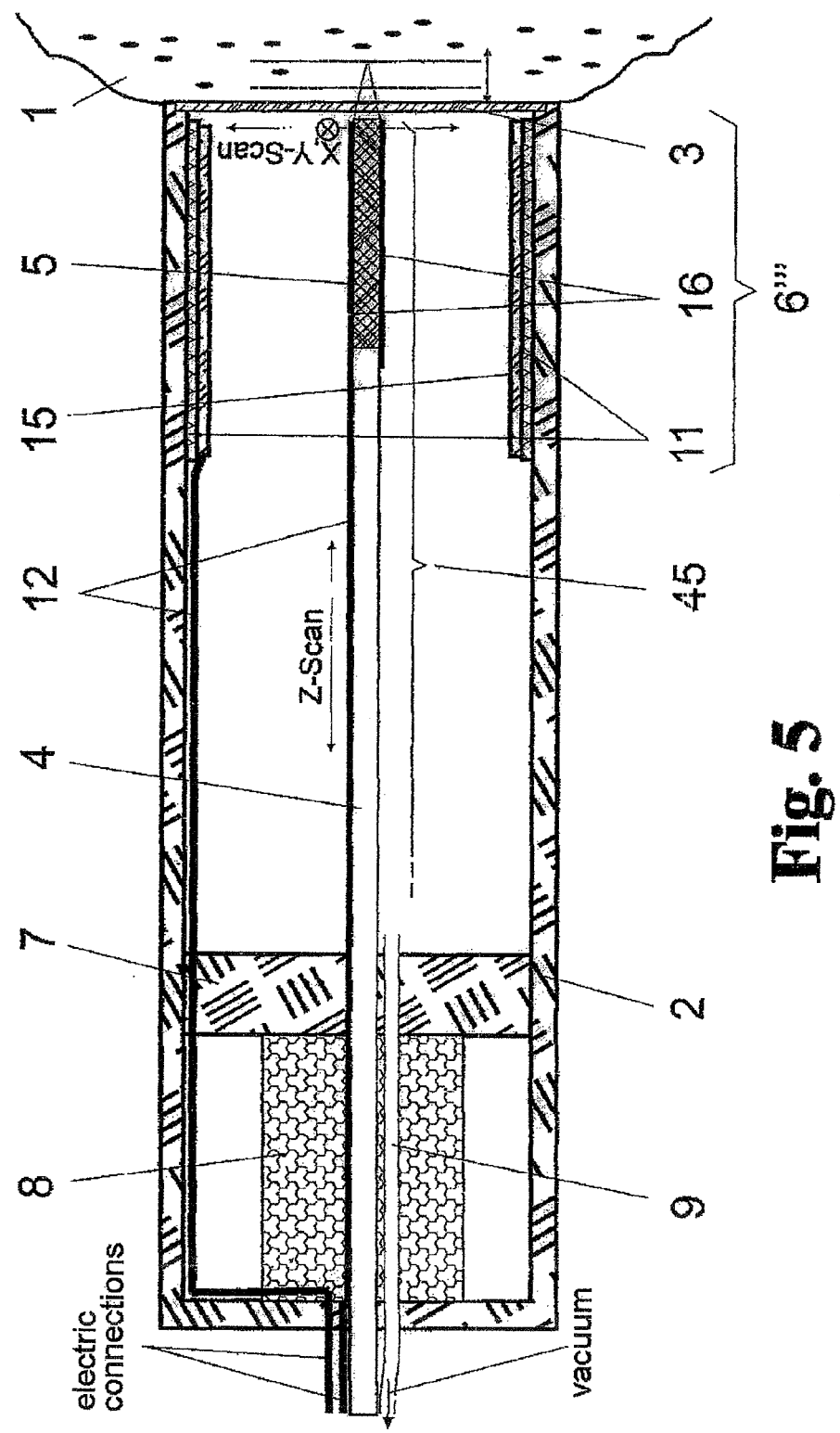
FIG. 5 shows a direct scanner according to FIG. 2a with an electromagnetic actuator and inductive elements on the fiber arrangement.

FIG. 5 shows another variant of this construction in which the permanent magnet 14 is replaced by a plurality of inductive elements 16. All of the other functions of the direct scanner are identical to those of the preceding constructions with the piezo scanner 6' or electrostatic scanner 6''.

When the embodiment examples according to FIGS. 2 to 5 and 9 are used for microscopic imaging, a so-called double-clad large-area core PCF (PCF=photonic crystal fiber) is used as fiber 4 as will be described in the following with reference to FIG. 10. A fiber 4 of this type has a central region 20 with an elevated refractive index $n_1$ whose leading characteristics are derived from a microstructured area 21 that is enclosed by a cladding 22 of optical material with a refractive index $n_2$. The cladding 22 is surrounded by an outer coating 23 with a low refractive index $n_3$ and improves the mechanical characteristics of the fiber 4 above all. Generally, $n_1 > n_2 > n_3$. The core area 20 is used to supply an active radiation to the object 1. The reaction radiation generated in the object 1 is coupled into the cladding 22 of the fiber 4 through the miniature focusing optics 5, guided back along the fiber 4, and coupled out by a beamsplitter 34 to an (external) photoreceiver 36 (both are shown only in FIG. 1). The photoreceiver 36 is outfitted with required color filters and, if necessary, with collecting optics. The object reaction radiation can take the form of reflecting or diffusely reflected excitation radiation, photoluminescence (particularly fluorescence), Raman scattering and Rayleigh scattering, generated harmonics (SHG, THG) of the excitation radiation, etc., depending on the specific application of the direct scanner. The fiber type mentioned above is also advantageous for applications in which imaging and tissue cutting are combined.

When the direct scanner is used exclusively for purposes of microsurgery or material cutting, the fiber 4 is preferably a large-area core PCF. In a fiber 4 of this type, the cladding 22 is reduced to the microstructured region 21, i.e., the cladding 22 shown in FIG. 10 is dispensed with in its entirety as a functional layer.

Figure 6:
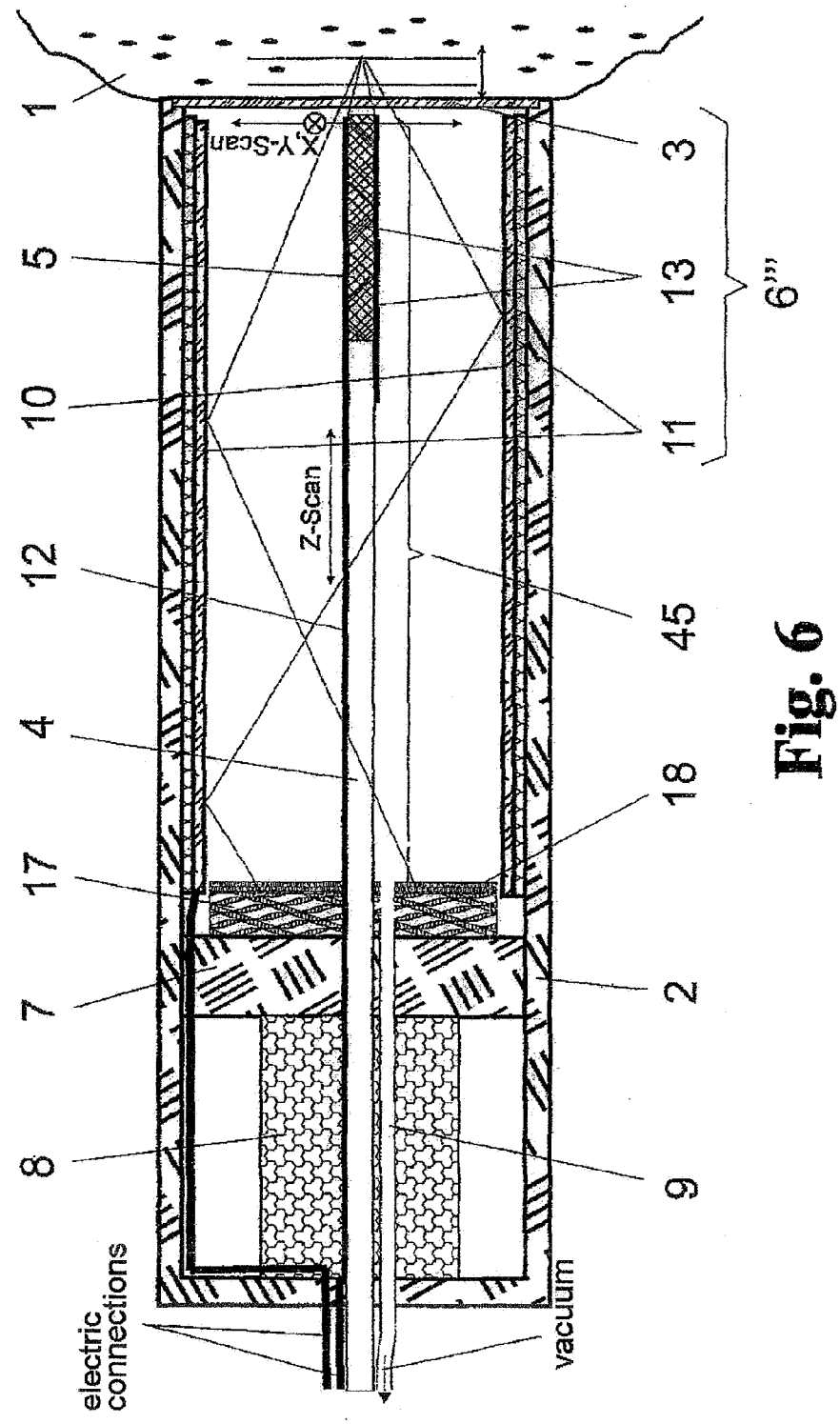
FIG. 6 shows a direct scanner with an electrostatic actuator, a receiver (with fiber passage) located directly in the scanner, and a reflecting layer at the housing walls.
Figure 7:
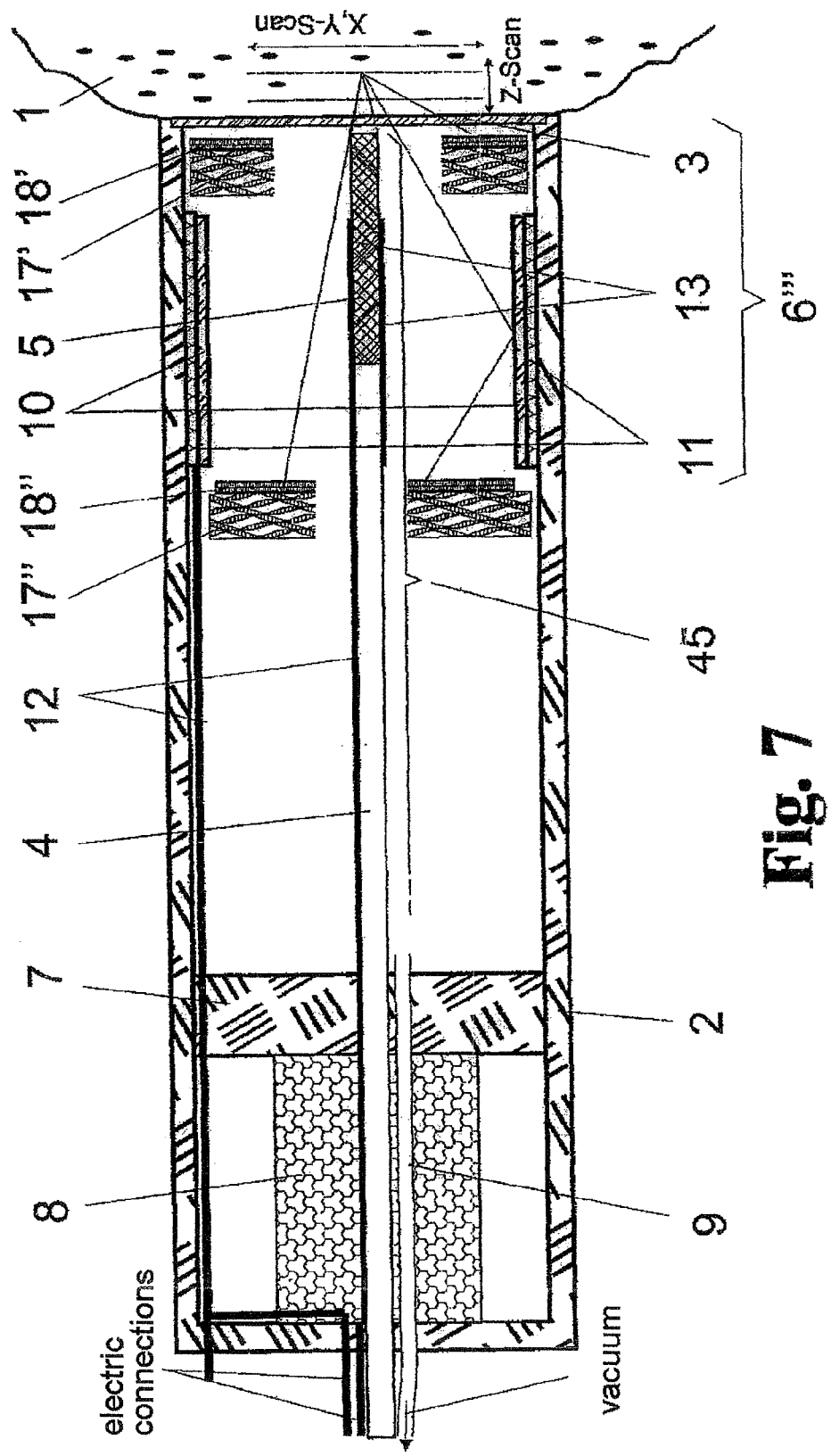
FIG. 7 shows a direct scanner with an electrostatic actuator and two directly integrated receivers.
Figure 8:
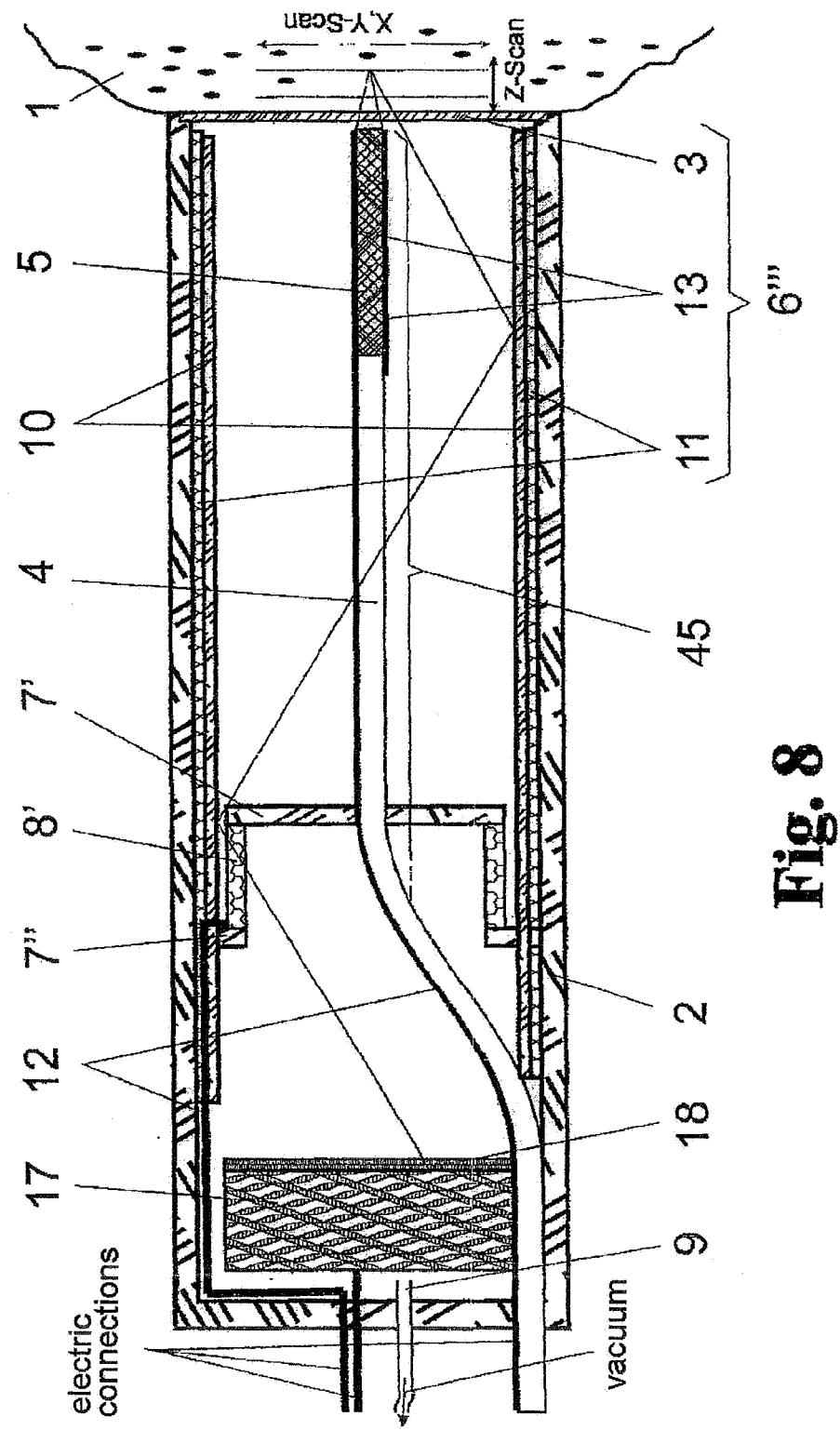
FIG. 8 shows a direct scanner with an electromagnetic actuator and a directly integrated receiver (without fiber passage)

FIGS. 6 to 8 show additional possibilities for detecting the object reaction radiation. The direct scanner works with electrostatic or electromagnetic actuators 6'' and 6''', respectively, in a special construction.

In a first construction according to FIG. 6, a large-area core PCF is used for the fiber 4. The object reaction radiation brought about by the active radiation is detected inside the direct scanner by a photoreceiver 17 preceded by an optical filter combination 18 which comprises at least one color filter. The inner walls of the housing 2 on the distal side of the photoreceiver 17 are provided with a mirror coating 10 which can also be formed, by way of substitution, by (reflecting) electrodes on the dielectric layer 11. This constructional variant is advantageous for miniaturized applications in which the photoreceiver 17 has a central hole for the fiber 4.

FIG. 7 discloses a construction in which at least two photoreceivers 17' and 17'' are arranged in such a way that as much object reaction radiation as possible is detected by the photoreceivers 17', 17'' without reflections at the walls of the housing 2 through filter combinations 18' and 18''. The photoreceivers 17', 17'' and the filter combinations 18', 18'' can be identical or different depending on the specific application.

FIG. 8 shows an alternative construction for photoreceivers 17 which do not have a central passage, e.g., secondary electron multipliers (SEM or PMT). In this arrangement, the fiber 4 is fastened in an axially movable frame 7' having a cross-web design. Accordingly, the frame 7' produces only minimal shadows on the photoreceiver 17. The frame 7' is fastened to an annular or axially segmented adjusting unit 8' which is connected in turn to a stationary annular or segmented element 7''.

A double-clad large-area core PCF can also be used as a fiber 4 in all of the constructional variants according to FIGS. 6 to 8 when a portion of the object reaction radiation must be guided through the fiber 4 to the external photoreceiver 36.

Figure 9:
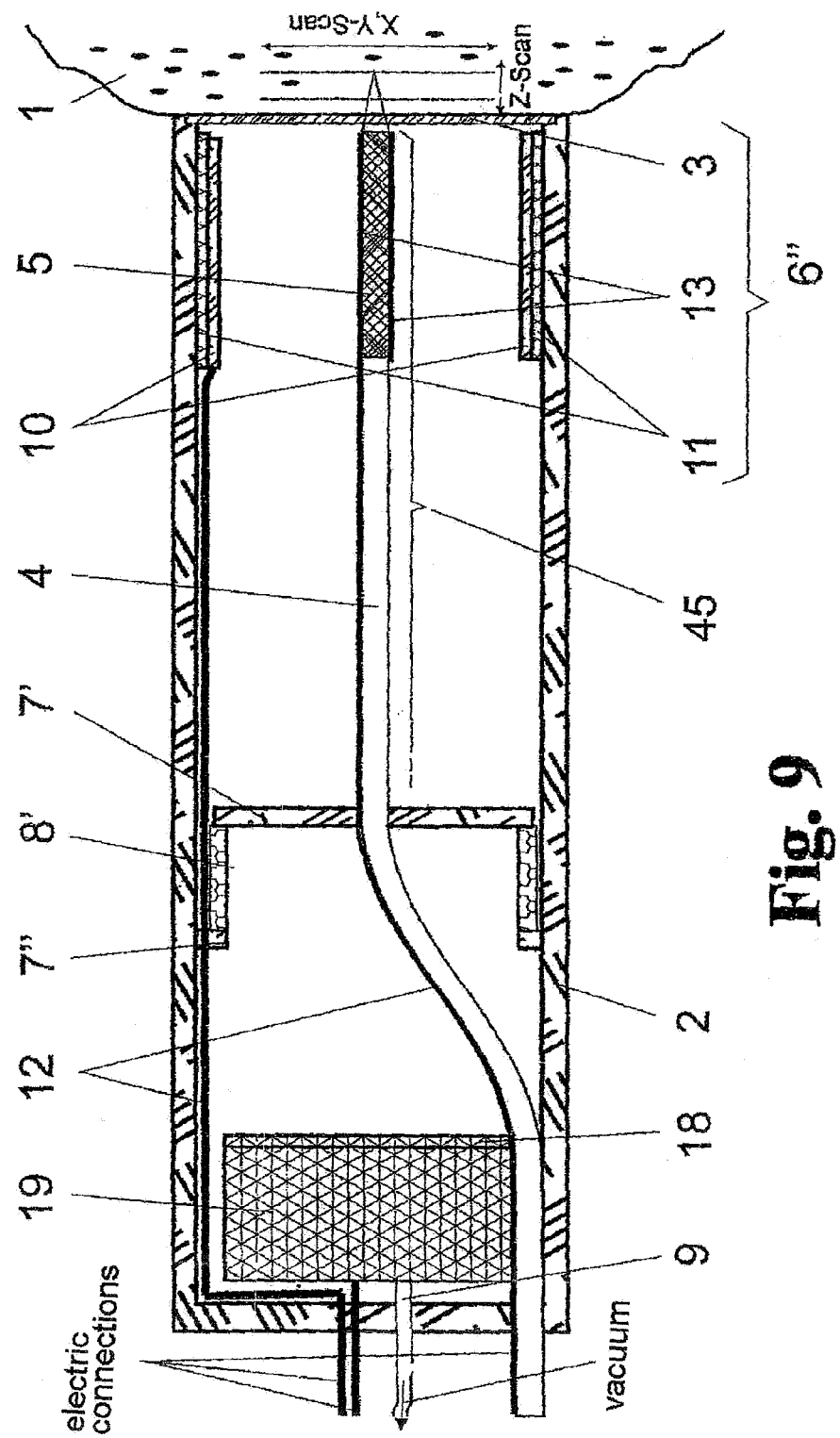
FIG. 9 shows a direct scanner with an electromagnetic actuator and detection of fluorescence through a fiber with a brightfield imaging arrangement (without fiber passage)
Figure 10:
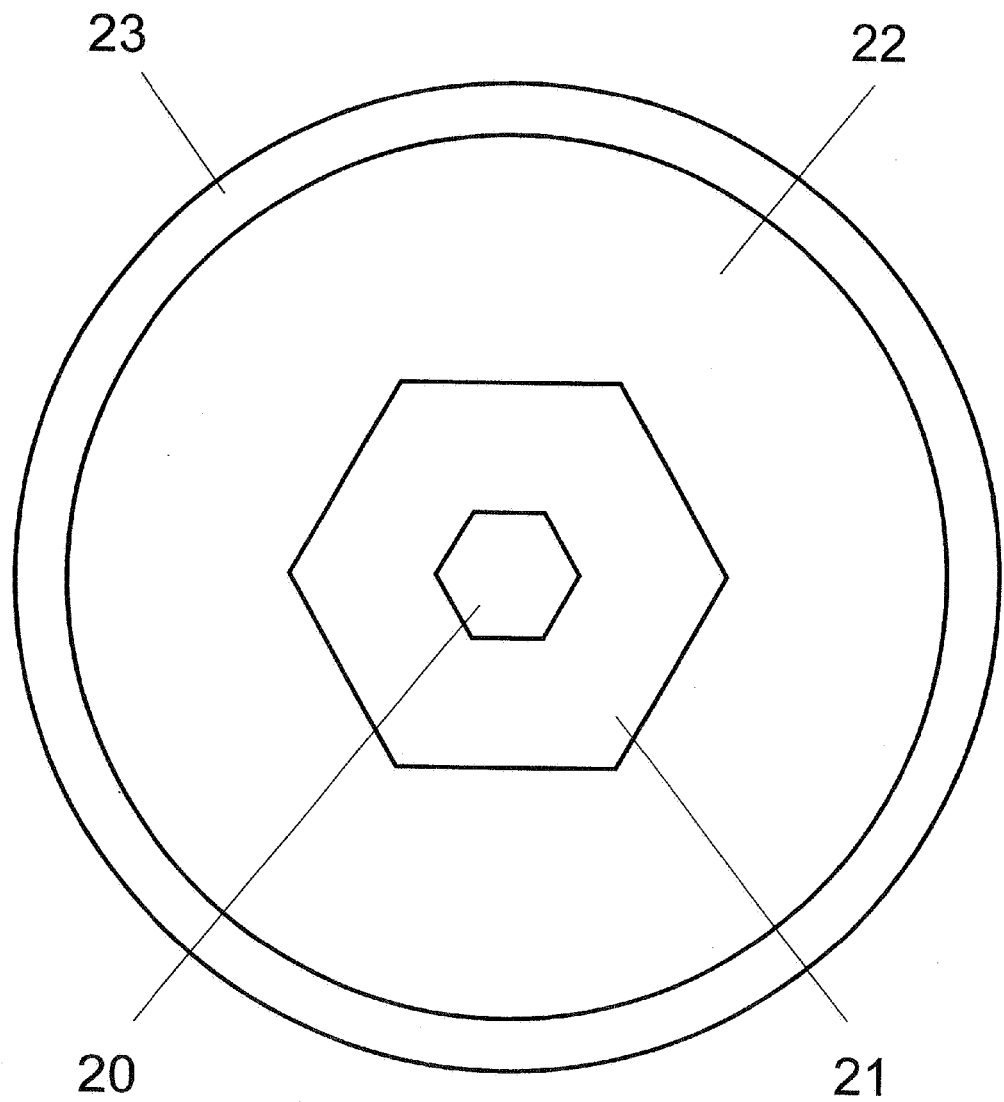
FIG. 10 shows a double-clad large-area core PCF type fiber.

FIG. 9 shows a construction in which the direct scanner with an electrostatic actuator 6'', formed of layer electrodes 10, dielectric layer 11, feed line 12 and conductive coating 13, can be combined with a two-dimensional image sensor 19, e.g., a CCD camera, including associated optics and illumination. In this arrangement, the fiber 4 is formed by a double-clad large-area core PCF which can be used for imaging as well as for microsurgical or material cutting purposes.

In all of the embodiment examples of the direct scanner according to FIGS. 6 to 9, a permanent magnet 14 and inductive elements 15, as shown in FIG. 4, can also be used as the electrostatic actuator 6'' in place of the conductive coatings 10 and 13 for moving the fiber focusing optics unit 45, or inductive elements 15 and 16 arranged at the housing 2 and at the fiber focusing optics unit 45 can be used as is shown in FIG. 5.

2. Direct Scanner with a Plurality of Fiber Focusing Optics Units

Figure 11:
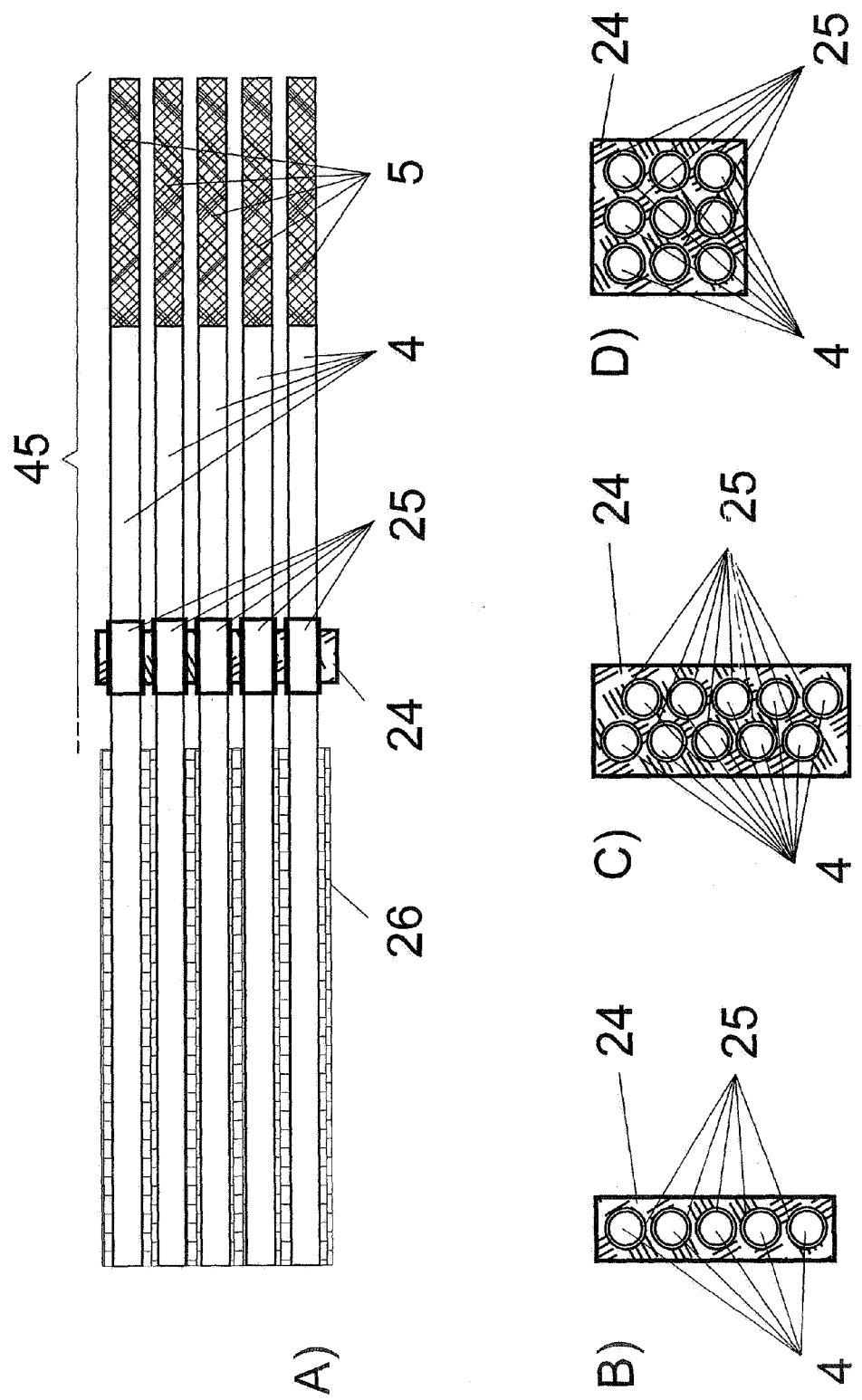
FIG. 11 is a schematic view of a multichannel arrangement in a housing.

The direct scanner can also be constructed as a multichannel device. In this construction, the fiber focusing optics unit 45 is replaced by a type of multicore cable as is shown in FIG. 11, at least two fiber focusing optics units 45 being connected to one another. The fibers 4 are embedded in a flexible band 26, and the freely projecting distal fiber portions are preferably of equal length and are secured in a holder 24 by stiffening elements 25. The stiffening elements 25 are used for adjusting oscillation characteristics of the distal portions of the fiber focusing optics unit 45. They can also be used for directly securing the individual miniature focusing optics 5.

Depending on the application, the fibers 4 are arranged symmetrically or asymmetrically in a geometric pattern through the holder 24, e.g., in a row (FIG. 11b) or in two rows (FIG. 11C) or as a matrix (FIG. 11D). Other geometric patterns are also possible depending on the application.

Depending on the application, the focusing optics 5 can be used in a straight-line variant (FIG. 2a) or an angled variant (FIG. 2b). The fiber holder 24 is fixedly connected to the scan actuator 6 or specifically to a piezo actuator 6' (FIG. 2a and FIG. 2b, respectively) or integrated in the axially movable scanner holder or frame holder 7 or 7', respectively (constructional variants according to FIGS. 3 to 5 and 9).

The type of fiber 4 that is used depends upon the application, e.g., double-clad large-area core PCF are advantageously used for MPI and large-area core PCF is sufficient for other applications.

2.1 Multichannel Scanning Imaging

In a modified construction, the direct scanner can be used as a multichannel scanner for multichannel-scanned imaging, e.g., LSM, MPI or OCT. In this case, all fiber focusing optics combinations 45 are moved synchronously over allocated partial areas by a two-dimensional scan actuator 6. The complete image is assembled from the partial images conveyed through the individual fibers 4. This is achieved by means of a uniform focal length of all of the individual miniature focusing optics 5 and a homogeneous output distribution of the excitation radiation.

By means of the parallel scanning of a plurality of fiber focusing optics unit 45, the image recording time is substantially shortened—this can result in the elimination of various artifacts caused by heartbeat, respiration or possible trembling of the examined object and/or patient. The imaging resolution can also be substantially increased in this way in the same recording time, or the total imaged area can be enlarged.

A possible depth adjustment is carried out as was described with reference to FIGS. 2 and 3.

2.2 Direct Multiphoton Tomography

In another construction, the multichannel direct scanner is comparable to example 2.1, but the focal lengths of the focusing optics 5 differ from those of individual fibers 4 (or groups of fibers) so that simultaneous images (tomograms) of at least two planes lying at different depths in the object 1 are recorded. Accordingly, a three-dimensional image of an object 1 can be recorded in one step, e.g., by LSM or MPI. Further, the recording time for tomograms at greater depth ranges or with a higher depth resolution (a plurality of imaging planes) can be substantially reduced by using depth adjustment so that the artifacts mentioned in example 2.1 can be eliminated in turn.

2.3 Direct Scanner Using Different Imaging Methods and/or Measuring Methods

In another construction, the multichannel direct scanner can be constructed as in examples 2.1 or 2.2; however, the individual fibers 4 (or groups of fibers) are provided with different focusing optics 5. The latter are used in parallel for different optical imaging methods or measuring methods, e.g., for simultaneous or fast sequential MPI or MP-tomography and OCT. In this case, the fiber focusing optics units 45 are optimized for the corresponding imaging method or measuring method and their oscillatory characteristics are adapted to one another.

The multichannel direct scanner can also be used for simultaneous measurement of different characteristics of the object reaction radiation, e.g., fluorescence polarization, coherence or object imaging, by means of these optimized, adapted characteristics.

2.4 Multichannel Direct Scanner with Combined Imaging and Cutting Function

In a multifunctional construction, the multichannel direct scanner is constructed according to one of the examples 2.1 and 2.3, but the focusing optics 5 of individual fibers 4 or groups of fibers and fiber 4 are different. Some of the fiber focusing optics combinations 4, 5 are optimized for imaging (e.g., by LSM or MPI) and the others are optimized for microsurgery or material processing (e.g., with multiphoton laser ablation). Therefore, imaging and processing can be carried out in parallel or in fast alternation by means of different fiber focusing optics units 45 or whole groups thereof.

2.5 Combination of a Plurality of Individual Fiber Direct Scanners

By joining preferably identical variants of the direct scanner according to FIGS. 2 to 9 in that the housings 2 of the individual scanners are rigidly connected to one another (not shown separately), either the surface of the object 1 which can be scanned in high resolution is enlarged, e.g., parallel MPI, or a multichannel device is provided, e.g., OCT multichannel direct scanner.

The arrangements described above are preferably used to carry out operations in the middle and posterior portions of the eye, particularly for cutting the lens in such a way that the elasticity can be improved by means of precise cuts, the retina can be cut in a precise manner, vessels can be closed or removed in age-related macular degeneration, unwanted cells can be removed or deactivated, channels can be drilled for relieving pressure, and complicated procedures can be carried out on the optic nerve.

Further, arrangements according to embodiment examples 1 to 4 can be used to carry out precise operations in the area of the middle ear.

Also, the constructions 1 to 4 according to the invention are used for operations in the brain area with high precision and minimal invasive action, e.g., to deactivate tumor cells optically without damaging neighboring areas of the brain.

Further, constructions 1 to 4 can advantageously be used to carry out operations in the region of the spinal column without damaging neighboring nerves.

The arrangements in embodiment examples 1 to 4 are also advantageously used to deactivate and remove unwanted cells and microorganisms in tissue-engineered skin products or to carry out operations within an embryo with high precision.

Arrangements according to the above examples 1 to 4 are particularly suitable for carrying out micro-cutting in an aqueous medium, particularly for realizing optical transfections for molecular transfer (e.g., of DNA) inside the body or to optically deactivate injected stem cells which differentiate in an unwanted manner.

REFERENCE NUMBERS

1 object
2 housing
2' housing cover
2" flexible tube
3 window
4 (optical) fiber
45 fiber focusing optics unit
5 miniature focusing optics
5' (refractive) spherical lens segment
5" first (object-side) GRIN lens
5''' second GRIN lens
5\* diffractive optics
**5\*\*** deflecting element
6 scan actuator
6' piezo scanner
6" electrostatic actuator
6''' electromagnetic actuator
7 axially movable scanner holder
7' axially movable frame holder
7" stationary frame holder
8 axial adjusting unit
8' annular axial adjusting unit
9 vacuum line
10 layer electrodes
11 dielectric layer
12 line
13 conductive coating
14 permanent magnet
15, 16 inductive element
17, 17', 17" photoreceiver
18, 18', 18" filter combination
19 (area) image sensor
20 central area
21 microstructured area
22 cladding
23 outer coating
24 fiber holder
25 stiffening element
26 flexible band
30 illumination and detection device
31 femtosecond laser
32 shutter
33 attenuator
34 (dichroic) splitter mirror
35 microscope optics
36 photon detector (PMT)
37 computer (PC)

What is claimed is:

1. A method for generating high-resolution microscopic images in the microendoscopy based on laser-induced object reaction radiation, comprising the following steps: focusing pulsed excitation radiation from a laser system into an object by means of a transmission focusing optics unit comprising a transmission system and miniature focusing optics having a high numerical aperture greater than 0.55 which are rigidly connected to the end of the transmission system to trigger a local reaction radiation of the object in the micrometer to nanometer range; executing a scanning movement by the distal end of the transmission focusing optics unit in at least two dimensions for the successive spatially changed position of the excitation radiation relative to the object and for locally allocated receiving high resolution object reaction radiation according to the locally changed position of the object present at the distal end of the miniature focusing optics; and transmitting the object reaction radiation which is scanned in a locally progressive manner by the transmission focusing optics unit to an image-generating system with a photon detectors wherein a third scanning process is carried out orthogonal to the two-dimensional scanning movement by axial movement of the transmission focusing optics unit for changing the depth of an image recording of the object reaction radiation generated from the two-dimensional scanning movement into a focal plane predetermined by the miniature focusing optics.

2. A method for generating high-resolution microscopic images in the microendoscopy based on laser-induced object reaction radiation, comprising the following steps: focusing pulsed excitation radiation from a laser system into an object by means of a transmission focusing optics unit comprising a transmission system and miniature focusing optics having a high numerical aperture greater than 0.55 which are rigidly connected to the end of the transmission system to trigger a local reaction radiation of the object in the micrometer to nanometer range; executing a scanning movement by the distal end of the transmission focusing optics unit in at least two dimensions for the successive spatially changed position of the excitation radiation relative to the object and for locally allocated receiving high resolution object reaction radiation according to the locally changed position of the object present at the distal end of the miniature focusing optics; and transmitting the object reaction radiation which is scanned in a locally progressive manner with a photon detector; wherein the miniature focusing optics and an optical fiber which produces an optical coupling with the laser system and the image-generating system are moved simultaneously in a scanning manner by means of a rigid connection as a transmission focusing optics unit, and wherein imaging and cutting functions are carried out on the object in a quasi-simultaneous manner by a type of fiber bundle comprising a plurality of fiber focusing optics units in that the excitation radiation is used for tissue cutting by changing parameters.

3. The method according to claim 2, wherein a multichannel scanning of the object is carried out simultaneously by a type of fiber bundle comprising a plurality of fiber focusing optics units.

4. The method according to claim 1, wherein the excitation radiation is switched to an increased-output active radiation in that the active radiation which is focused by means of the transmission focusing optics unit is pulsed into the object for triggering local tissue changes, and wherein the distal end of the transmission focusing optics unit is moved in a defined manner for carrying out three-dimensional cutting steps in the object.

5. The method according to claim 4;
wherein switching for beaming in the increased-output active radiation, for tissue cutting of the object is carried out alternately with the scanned beaming in of reduced-output excitation radiation for spatially-resolving image recording of object reaction radiation.

6. The method according to claim 4;
wherein the radiation emitted by the object is detected by means of time-correlated single-photon counting.

7. A method for microprocessing of biological material utilizing a miniaturized microscopic head in laser endoscopy with a precision under one micrometer, comprising:
coupling laser pulses of a femtosecond laser with a pulse energy of from 0.05 nJ to 100 µJ via the fiber into the miniature focusing optics being arranged on the object side of the fiber and having a high numerical aperture, and focusing the laser pulses on a target inside the object with an illumination spot of less than 10 µm;
triggering multiphoton processes in the form of a target ionization, an optical breakdown and plasma formation by transient intensities of the laser pulses greater than 100 GW/cm$^2$ which are used for endoscopic micro-processing with an accuracy under 100 µm without the occurrence of significant collateral damage in neighboring areas; and
detecting the plasma radiation and other object reaction radiation emitted by the target by an illumination and detection device in an image-generating manner in order to monitor the micro-processing.

8. The method according to claim 7;
wherein individual cells within tissue are destroyed optically by single point illumination without damaging neighboring cells, where the diameter of the destroyed area is varied through the selection of the exposure time and the laser pulse energy that is used.

9. The method according to claim 7;
wherein a precise cut with cut widths of less than 10 µm is carried out in the interior of an object by means of a linear movement, where the width of the cut is varied through the selection of exposure time and laser pulse energy.

10. The method according to claim 7;
wherein a precise removal of material is realized on larger areas of 100 µm$^2$ to 1 mm$^2$ with a precision of under 10 µm and a depth action of under 20 µm when a region (ROI) is scanned.

11. The method according to claim 7;
wherein a large-volume material removal in the range of 1 µm$^3$ to 1000 mm$^3$ is realized by scanning a region (ROI) and displacing the focal plane.

12. A miniaturized microscopic head for endoscopic applications, comprising:
transmission optics for supplying an excitation radiation;
focusing optics for introducing bundled excitation radiation into an object;
a scanning device for changing the location of the energy input; and
a housing;
wherein said focusing optics, said scanning device, and an end of said transmission optics are arranged in the housing, where the focusing optics focus the active radiation into the object through a window in the housing;
wherein said focusing optics are miniature focusing optics which have a diameter of less than 2 mm and a numerical aperture of NA>0.55, where the excitation radiation is focused by the immature focusing optics so as to be limited locally on an area of less than 100 µm in the object;
wherein said end of the transmission optics in the housing is rigidly connected to said miniature focusing optics, with both forming a transmission focusing optics unit; and
wherein said scanning device has at least one scan actuator for lateral movement of the transmission focusing optics unit, which scan actuator is arranged to cause a two-dimensional movement of the focusing optics in a plane in the immediate vicinity of the window of the housing.

13. The miniaturized microscopic head according to claim 12;
wherein the scanning device further has an axially movable adjusting unit for axial movement of the transmission focusing optics unit, wherein the transmission focusing optics unit is clamped in the adjusting unit so as to be fixed axially.

14. The miniaturized microscopic head according to claim 12;
wherein the transmission focusing optics unit is rigidly assembled from the miniature focusing optics and an optical fiber, wherein the transmission focusing optics unit is clamped in the adjusting unit so as to be fixed axially.

15. The miniaturized microscopic head according to claim 12;
wherein the transmission focusing optics unit is rigidly assembled from the miniature focusing optics and a reflective waveguide, wherein the transmission focusing optics unit is clamped in the adjusting unit so as to be fixed axially.

16. The miniaturized microscopic head according to claim 12;
wherein the transmission focusing optics unit comprises the miniature focusing optics and microscope optics of a illumination and detection device, wherein the two-dimensional scan actuator and the axial adjusting unit are connected exclusively to the miniature focusing optics.

17. The miniaturized microscopic head according to claim 12;
wherein the focusing optics are GRIN optics with a rounded end face.

18. The miniaturized microscopic head according to claim 12;
wherein the focusing optics are GRIN optics preceded by a refractive spherical lens segment.

19. The miniaturized microscopic head according to claim 12;
wherein the focusing optics contain two-lens GRIN optics and diffractive optics.

20. The miniaturized microscopic head according to claim 12;
wherein the axial adjusting unit is rigidly connected to the two-dimensional scan actuator and the scan actuator is fastened in an axially movable scanner holder.

21. The miniaturized microscopic head according to claim 14;
wherein the transmission optics comprise a microstructured double-clad large-area core photonic crystal fiber which transmits the femtosecond laser radiation virtually without dispersion.

22. The miniaturized microscopic had according to claim 14;
wherein the transmission optics comprise a large-area core photonic crystal fiber.

23. The miniaturized microscopic head according to claim 14;
wherein at least one photoreceiver is arranged around the fiber in the housing for directly receiving the object reaction radiation.

24. The miniaturized microscopic head according to claim 14;
wherein a plurality of photoreceivers are arranged around the fiber in the housing for directly receiving different spectral components of the object reaction radiation.

25. The miniaturized microscopic head according to claim 14;
wherein a plurality of fibers are guided in parallel in a fiber holder in the housing.

26. The miniaturized microscopic head according to claim 25;
wherein the fibers are embedded in a flexible band and have stiffening elements for suppressing oscillation.

27. The miniaturized microscopic head according to claim 12;
wherein the housing is tubular and is hermetically sealed at its end sides by a cover and a window.

28. The miniaturized microscopic head according to claim 12;
wherein the housing has at least one plane side wall, wherein a window is arranged laterally in the plane side wall of the housing and the housing is hermetically sealed by end covers.

29. The miniaturized microscopic head according to claim 28;
wherein the miniature focusing optics have a radiation-deflecting element so that the excitation radiation exits laterally from the transmission focusing optics unit and can be focused on the object through the laterally arranged window; and
wherein the adjusting unit is provided for a first lateral scan dimension at the object and the scan actuator is provided for a second lateral scan dimension and for the depth scan in the object.

30. The miniaturized microscopic head according to claim 27;
wherein the hermetically sealed housing is evacuated.

* * * * *